(12) United States Patent
Shah et al.

(10) Patent No.: US 10,576,031 B1
(45) Date of Patent: Mar. 3, 2020

(54) EXFOLIATING AND HYDRATING MAKEUP REMOVING COMPOSITIONS

(71) Applicant: L'OREAL, Paris (FR)

(72) Inventors: Anil Shah, East Windsor, NJ (US); Stan Najmr, Rahway, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/139,878

(22) Filed: Sep. 24, 2018

(51) Int. Cl.
| | | |
|---|---|---|
| *A61K 8/34* | (2006.01) | |
| *A61K 8/60* | (2006.01) | |
| *A61K 8/37* | (2006.01) | |
| *A61K 8/92* | (2006.01) | |
| *A61Q 19/10* | (2006.01) | |
| *A61Q 1/14* | (2006.01) | |
| *A61Q 19/00* | (2006.01) | |

(52) U.S. Cl.
CPC .............. *A61K 8/345* (2013.01); *A61K 8/375* (2013.01); *A61K 8/60* (2013.01); *A61K 8/922* (2013.01); *A61K 8/925* (2013.01); *A61Q 1/14* (2013.01); *A61Q 19/10* (2013.01); *A61K 2800/10* (2013.01); *A61K 2800/28* (2013.01); *A61K 2800/31* (2013.01); *A61K 2800/34* (2013.01); *A61Q 19/001* (2013.01)

(58) Field of Classification Search
CPC .......... A61K 8/345; A61K 8/375; A61K 8/80; A61K 2800/10; A61K 2800/28; A61Q 1/14
See application file for complete search history.

(56) References Cited

U.S. PATENT DOCUMENTS

| | | | |
|---|---|---|---|
| 5,928,653 A | 7/1999 | Vanstraceele et al. | |
| 6,162,451 A | 12/2000 | Vanstraceele et al. | |
| 6,528,071 B2 * | 3/2003 | Vatter | A61K 8/26 |
| | | | 424/401 |
| 8,440,211 B2 | 5/2013 | Auguste | |
| 8,685,907 B2 | 4/2014 | Poletti | |
| 2009/0074689 A1 | 3/2009 | Auguste | |
| 2010/0112100 A1 | 5/2010 | Willemin et al. | |
| 2010/0210498 A1 | 8/2010 | Poletti | |
| 2016/0175222 A1 | 6/2016 | Pavel et al. | |
| 2017/0239166 A1 | 8/2017 | Daubersies et al. | |
| 2017/0246103 A1 * | 8/2017 | Argembeaux | A61K 8/41 |

OTHER PUBLICATIONS

Glyceryl Monoesters (https://web.archive.org/web/20170926233616/https://cosmeticsinfo.org/ingredient/glyceryl-stearateacetate) available Sep. 26, 2017, pp. 1-2 (Year: 2017).*
Trihydroxystearin (https://www.ewg.org/skindeep/ingredient/706663/Trihydroxystearin/), available Sep. 20, 2017, pp. 1-2 (Year: 2017).*
PG6PR (http://www.ewg.org/skindeep/ingredient/705042/Polyglyceryl-6_Polyricinoleate/), available Feb. 26, 2016, pp. 1-2 (Year: 2016).*
Ethylhexyl Palmitate (https://www.ewg.org/skindeep/ingredient/702348/ETHYLHEXYL_PALMITATE/), available Jan. 28, 2017, pp. 1-3 (Year: 2017).*
"Super Stay Eraser Lip Color Remover", Maybelline https://www.ulta.com/superstay-eraser-lip-color-remover?productId=xlsImp-prod16211183.
"Pure-Sugar; Nourish & Soften Cocoa Scrub", L'Oreal https://www.lorealparisusa.com/beauty-magazine/skin-care/skin-care-essentials/what-is-a-sugar-scrub.aspx.

* cited by examiner

Primary Examiner — Andrew S Rosenthal
(74) Attorney, Agent, or Firm — Polsinelli PC

(57) ABSTRACT

The present disclosure relates to a makeup removing composition comprising: (a) about 5 to about 50 wt. % of exfoliating particles; (b) about 5 to about 30 wt. % of glycerin; (c) about 1 to about 50 wt. % of one or more natural fatty compounds; and (d) about 25 to about 75 wt. % of one or more nonionic surfactants; wherein the weight percentages are based on the total weight of the composition. In addition to effectively removing makeup, the composition both exfoliates and hydrates the skin. Accordingly, the disclosed includes method for removing makeup from the skin and/or methods for exfoliating and hydrating the skin.

17 Claims, No Drawings

EXFOLIATING AND HYDRATING MAKEUP REMOVING COMPOSITIONS

BACKGROUND

Modern makeup technologies are increasingly innovative. Consumers seek durable cosmetics such as long-lasting lipsticks, non-transfer foundations, and waterproof makeup for the face and eyes. Colorants are used in these cosmetics to highlight the lips and other skin regions on the body. Most conventional lipstick formulations, for example, have a semisolid consistency, and include a colorant such as a pigment mixed with an oily vehicle such as a fat or oil stiffened to a desired consistency with one or more waxes. Lipsticks having a long-lasting color have been developed that lessen the need for frequent reapplication and to avoid problems such as the lipstick rubbing off from the lips and onto clothing.

There are various methods for increasing the long-lastingness of cosmetics. For example, increasing the concentration of colorants in can increase the long-lastingness of a cosmetic. However, increasing the concentration of colorants often results in the cosmetic becoming dry more quickly and can results in a loss of luster. Moisturizers and conditioning agents are can be added to the formulations, but these components may undermine durability. Various polymers and copolymers can also be used in cosmetics to improve durability. Polymer and copolymers can form a strong adhesive film that is not easily removed from the skin.

Durable cosmetics are continuously being developed and are purposely difficult to remove. Therefore, makeup removing products are needed to effectively remove them. Effective makeup removing products, however, tend to be harsh, can injure the skin, and include non-natural ingredients. Consumers desire cosmetics that are free of unnatural substances, preferring instead ingredients of natural origin, renowned for their better tolerance and affinity for the skin, and are environmentally friendly. There exists an increased consciousness amongst consumers regarding the types of ingredients used in consumer products, including cosmetics. One of the biggest impetus for seeking natural or organic products is the perceived health benefits. Those who use make-up remover are likely wearing make-up on a regular basis, and therefore seek the most safe and effective methods for easily removing the makeup.

SUMMARY OF THE DISCLOSURE

The instant disclosure is directed to makeup removing compositions. The compositions effectively remove makeup from the skin including the skin of the lips, while simultaneously providing exfoliating and hydrating properties. The technology simplifies the user's routine by providing benefits such as exfoliation and hydration to the skin while efficiently removing makeup. The makeup removing compositions include exfoliating particles, glycerin, natural fatty compounds, nonionic surfactants, etc. The natural fatty compounds have delaminating properties that break up the makeup adhered to the skin, while the exfoliating particles scrub away the makeup and dead skin that may be present. The glycerin, especially in combination with the other components of the composition, provides hydrating properties.

The makeup removing compositions typically include:
(a) exfoliating particles;
(b) glycerin;
(c) one or more natural fatty compounds; and
(d) one or more nonionic surfactants; wherein the weight percentages are based on the total weight of the composition.

The compositions may be anhydrous or essentially anhydrous. Additionally, the makeup removing compositions do not require synthetic ingredients. Thus, the makeup removing compositions may be free or essentially free of synthetic ingredients, e.g., silicones, petroleum based products such as petrolatum, plastics, alkoxylated compounds, etc. In particular, the makeup removing compositions may be "natural" compositions.

The makeup removing compositions are useful in methods for removing makeup from the body, in particular the face, including the lips. The user can simply apply the makeup removing compositions to an area of the body having makeup applied thereon, and subsequently remove the composition along with the makeup, for example, by wiping it away with a tissue or rinsing it away with water. The user can also gently massage or rub the makeup removing composition against the skin to help facilitate the makeup removing action and enhance the exfoliation process.

DETAILED DESCRIPTION OF THE DISCLOSURE

The makeup removing compositions of the instant disclosure effectively remove makeup from the skin, including the skin of the lips, while simultaneously providing exfoliating and hydrating properties to the skin. The makeup removing compositions, which may be anhydrous, typically include:
(a) about 5 to about 50 wt. % of exfoliating particles;
(b) about 1 to about 50 wt. % of glycerin;
(c) about 1 to about 50 wt. % of one or more natural fatty compounds; and
(d) about 25 to about 75 wt. % of one or more nonionic surfactants; wherein the weight percentages are based on the total weight of the composition.

The makeup removing compositions do not require synthetic ingredients and can be prepared from natural ingredients. Synthetic ingredients may be included in the makeup removing compositions but they are not required, and may be excluded. Accordingly, the makeup removing compositions may be free or essentially free of synthetic ingredients. The term "synthetic ingredients" means an ingredient that is purely synthetic, or not of natural origin, for example, silicones, various polymers, such as polymers made by radical polymerization of ethylenically unsaturated monomers or by polycondensation, etc. The term "natural ingredient" means an ingredient of natural origin, which includes those that have not been chemically or physically modified and those that have been chemically or physically modified, but retain at least 70% of their molecular structure from the original natural source. In particular, the term "natural ingredient" refers to one of the following:

1. An ingredient which remains unchanged from its natural state; or
2. An ingredient which has undergone chemical or other processing which modifies it from its natural state but which retains at least 70% of its molecular structure from the original natural source.

In general, a natural ingredient may be processed to improve its stability, efficacy, and/or safety. The degree of processing varies for each ingredient, but ultimately ingredients retaining at least 70% of their molecular structure from the original natural source are considered natural.

Makeup removing compositions that include only natural ingredients may be referred to as "natural makeup removing compositions." As indicated above, the degree of processing can vary for each ingredient so long as the ingredient retains at least 70% of its molecular structure from the original natural source. Nonetheless, in some cases, the makeup removing compositions may include ingredients that retain at least 70%, 75%, 80%, 85%, 90%, 95%, 96%, 97%, 98%, 99%, or 100% of their molecular structure from the original natural source.

Exfoliating Particles

Exfoliation involves the removal of the oldest dead skin cells on the skin's outermost surface. Exfoliating particles are particulate materials that retain their particulate nature in the makeup removing compositions. The particulate material is sufficiently durable and abrasive such that when rubbed against the skin, the mechanical force displaces at least a portion, and in some cases a majority of the oldest dead skin cells on the skin's outermost surface. Many different types of materials can be used as exfoliating particles. Exfoliating particles may be inorganic or organic, of plant or animal origin, or synthetic. Non-limiting examples of exfoliation particles include crystalline sugars and/or salts, polyethylene beads or powder, nylon powder, polyvinyl chloride powder, pumice, ground apricot kernel or walnut husk, sawdust, glass beads, alumina, and mixtures thereof.

It is preferable that the exfoliating particles are natural. Furthermore, in some instances, the exfoliating particles are preferably insoluble in an oily or fatty medium but soluble in water. Non-limiting examples of exfoliating particles that are insoluble in an oily or fatty medium but soluble in water include sugars and salts. The makeup removing compositions of the instant case are typically comprised of an oily or fatty medium, which is anhydrous or essentially anhydrous. Sugar and/or salt particles can be incorporated into these makeup removing compositions and retain their particulate nature. After application to the skin, upon contact with water, the salt and/or sugar particles dissolve and are easily rinsed or wiped away. Sugar particles can be particularly preferred by consumers due to their sweet taste. Sugar particles provide sweetness to the makeup removing compositions, in instances when the composition comes into contact with an area of the mouth and/or lips. This is foreseeable when the makeup removing compositions re used for removing lipstick. Non-limiting examples of useful sugars include sucrose, fructose, maltose, and dextrose, preferably sucrose and/or fructose.

The total amount of exfoliating particles in the makeup removing composition can vary but is typically from about 1 to about 50 wt. %, based on the total weight of the makeup removing composition. In some cases, the total amount of exfoliating particles may be from about 10 to about 50 wt. %, about 15 to about 50 wt. %, about 20 to about 50 wt. %, about 5 to about 40 wt. %, about 10 to about 40 wt. %, about 15 to about 40 wt. %, or about 20 to about 40 wt. %, based on the total weight of the makeup removing composition.

Glycerin

Glycerin (also referred to as glycyerine or glycerol) is a natural polyol that is essentially colorless and odorless, and is slightly sweet. Glycerin provides moisturizing and hydrating properties to the makeup removing compositions. The total amount of glycerin in the makeup removing compositions can vary but is typically from about 1 to about 50 wt. %, based on the total weight of the makeup removing composition. In some instances, the total amount of glycerin in the makeup removing compositions is from about 5 to about 50 wt. %, about 10 to about 50 wt. %, about 5 to about 45 wt. %, about 10 to about 45 wt. %, about 5 to about 40 wt. %, about 10 to about 40 wt. %, about 5 to about 35 wt. %, or about 10 to about 35 wt. %, based on the total weight of the makeup removing composition.

Fatty Compounds

The makeup removing compositions include one or more fatty compounds, preferably one or more natural fatty compounds. Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Useful fatty alcohols include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Useful fatty acids include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Non-limiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Useful fatty alcohol derivatives include alkyl ethers of fatty alcohols, alkoxylated fatty alcohols, alkyl ethers of alkoxylated fatty alcohols, esters of fatty alcohols and a mixture thereof. Non-limiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting examples of polyglycerol esters of fatty acids include those of the following formula:

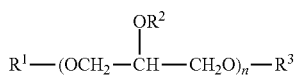

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate.

The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Non-limiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

The total amount of fatty compounds in the makeup removing compositions can vary but is typically about 1 to about 50 wt. %, based on the total weight of the makeup removing composition. In some cases, the total amount of fatty compounds may be from about 1 to about 40 wt. %, about 1 to about 30 wt. %, about 1 to about 20 wt. %, about 1 to about 10 wt. %, about 5 to about 50 wt. %, about 5 to about 40 wt. %, about 5 to about 30 wt. %, about 5 to about 20 wt. %, or about 5 to about 10 wt. %, based on the total weight of the makeup removing composition.

Natural Oils

In some embodiments, one or more fatty compounds of the makeup removing compositions are selected from natural oils. Non-limiting examples of suitable natural oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl tri acetyl hydroxystearate, glyceryl tri acetyl ricinoleate, glyceryl trioctanoate, hydrogenated castor oil, linseed oil, mink oil, olive oil, palm oil, castor oil, illipe butter, rapeseed oil, soybean oil, sunflower seed oil, pine oil, tallow, tricaprin, trihydroxystearin, triisostearin, trilaurin, trilinolein, trimyristin, triolein, tripalmitin, tristearin, walnut oil, wheat germ oil, cholesterol, essential oils (for example, peppermint oil), and mixtures thereof.

The total amount of natural oils in the makeup removing composition, if present, can vary but is typically about 0.01 to about 25 wt. %, based on the total weight of the makeup removing composition. In some cases, the total amount of natural oils may be about 0.01 to about 20 wt. %, about 0.01 to about 15 wt. %, about 0.01 to about 10 wt. %, about 0.01 to about 5 wt. %, about 0.1 to about 20 wt. %, about 0.1 to about 15 wt. %, about 0.1 to about 10 wt. %, about 0.1 to about 5 wt. %, or about 0.1 to about 2 wt. %, based on the total weight of the makeup removing composition.

Polyglycerol Esters

In some embodiments, one or more fatty compounds in the makeup removing compositions include one or more polyglycerol esters. Polyglycerol esters may be selected from Polyglyceryl-4 Caprate, Polyglyceryl-2 Caprate, Polyglyceryl-4 Caprylate, Polyglyceryl-6 Caprylate, Polyglyceryl-6 Caprate, Polyglyceryl-4 Caprylate/Caprate, Polyglyceryl-6 Caprylate/Caprate, Polyglyceryl-3 Cocoate, Polyglyceryl-4 Cocoate, Polyglyceryl-10 Decalinoleate, Polyglyceryl-10 Decaoleate, Polyglyceryl-10 Decacasterate, Polyglyceryl-3 Dicaprate, Polyglyceryl-3 Dicocoate, Polyglyceryl-10 Didecanoate, Polyglyceryl-2 Diisostearate, Polyglyceryl-3 Diisostearate, Polyglyceryl-10 Diisostearate, Polyglyceryl-4 Dilaurate, Polyglycerin-2 Dioleate, Polyglyceryl-3 Dioleate, Polyglyceryl-6 Dioleate, Polyglyceryl-10 Dioleate, Polyglyceryl-6 Dipalmitate, Polyglyceryl-10 Dipalmitate, Polyglyceryl-2 Dipolyhydroxystearate, Polyglyceryl-2 Distearate, Polyglyceryl-3 Distearate, Polyglyceryl-6 Distearate, Polyglyceryl-10 Distearate, Polyglyceryl-10 Heptaoleate, Polyglyceryl-10 Heptastearate, Polyglyceryl-6 Hexaoleate, Polyglyceryl-10 Hexaoleate, Polyglyceryl-2 Isopalmitate, Polyglyceryl-2 Isostearate, Polyglyceryl-4 Isostearate, Polyglyceryl-5 Isostearate, Polyglyceryl-6 Isostearate, Polyglyceryl-10 Isostearate, Polyglyceryl-2 Laurate, Polyglyceryl-3 Laurate, Polyglyceryl-4 Laurate, Polyglyceryl-4 Laurate/Sebacate, Polyglyceryl-4 Laurate/Succinate, Polyglyceryl-5 Laurate, Polyglyceryl-6 Laurate, Polyglyceryl-10 Laurate, Polyglyceryl-3 Myristate, Polyglyceryl-10 Myristate, Polyglyceryl-2 Oleate, Polyglyceryl-3 Oleate, Polyglyceryl-4 Oleate, Polyglyceryl-5 Oleate, Polyglyceryl-6 Oleate, Polyglyceryl-8 Oleate, Polyglyceryl-10 Oleate, Polyglyceryl-3 Palmitate, Polyglyceryl-6 Palmitate, Polyglyceryl-10 Pentalaurate, Polyglyceryl-10 Pentalinoleate, Polyglyceryl-4 Pentaoleate, Polyglyceryl-10 Pentaoleate, Polyglyceryl-3 Pentaricinoleate, Polyglyceryl-6 Pentaricinoleate, Polyglyceryl-10 Pentaricinoleate, Polyglyceryl-4 Pentastearate, Polyglyceryl-6 Pentastearate, Polyglyceryl-10 Pentastearate, Polyglyceryl-3 Polyrisinoleate, Polyglyceryl-6 Polyricinoleate, Polyglyceryl-3 Ricinoleate, Polyglyceryl-2 Sesquiisostearate, Polyglyceryl-2 Sesquioleate, Polyglyceryl-2 Sesquistearate, Polyglyceryl-3 Stearate, Polyglyceryl-2 Stearate, Polyglyceryl-4 Stearate, Polyglyceryl-8 Stearate, Polyglyceryl-10 Stearate, Polyglyceryl-2 Tetraisostearate, Polyglyceryl-6 Tetraoleate, Polyglyceryl-10 Tetraoleate, Polyglyceryl-2 Tetrastearate, Polyglyceryl-2 Triisostearate, Polyglyceryl-3 Triisostearate, Polyglyceryl-10 Trioleate, Polyglyceryl-4 Tristearate, Polyglyceryl Tristearate, Polyglyceryl-10 Tristearate, and a mixture thereof.

The total amount of polyglycerol esters in the makeup removing composition, if present, can vary but typically is about 0.01 to about 25 wt. %, based on the total weight of the makeup removing composition. In some cases, the total amount of polyglycerol esters may be about 0.01 to about 20 wt. %, about 0.01 to about 15 wt. %, about 0.01 to about 10 wt. %, about 0.01 to about 5 wt. %, about 0.1 to about 20 wt. %, about 0.1 to about 15 wt. %, about 0.1 to about 10 wt. %, or about 0.1 to about 5 wt. %, based on the total weight of the makeup removing composition.

Waxes Having a Melting Point of at Least 60° C.

In some embodiments, the makeup removing compositions include one or more waxes, in particular, one or more waxes having a melting point of at least 60° C. Wax(es) with a melting point of greater than or equal to 60° C. may be selected from carnauba wax, ozokerite, microcrystalline wax, 12-hydroxystearic acid, a polyethylene wax (for example those sold under the names Performalene 500 L Polyethylene or Performalene 400 L Polyethylene by New Phase Technologies, or Asensa SC 211 from Honeywell), polymethylene waxes (for example the product sold under the reference Cirebelle 108 by Cirebelle), beeswax, candelilla wax, hydroxyoctacosanyl hydroxystearate, hydrogenated castor oil, hydrogenated jojoba oil, rice bran wax, polyglycerolated beeswax, octacosanyl stearate, ceresin wax, $C_{20}$-$C_{40}$ alkyl (hydroxystearyloxy)stearate waxes, 12-hydroxystearic acid, polyethylene alcohol wax, Fischer-Tropsch wax, the waxes obtained by hydrogenation of castor oil esterified with cetyl alcohol, ouricury wax, montan wax, the glyceryl trihydroxystearate whose INCI name is Trihydroxystearin (sold, for example, by Elementis under the name Thixcin R), and mixtures thereof.

Preferably, the waxes have a melting point of greater than or equal to 65° C. are chosen from carnauba wax, ozokerite, microcrystalline wax, 12-hydroxystearic acid, a polyethylene wax (for example those sold under the names Performalene 500 L Polyethylene or Performalene 400 L Polyethylene by New Phase Technologies), candelilla wax, hydroxyoctacosanyl hydroxystearate, hydrogenated castor oil, hydrogenated jojoba oil, rice bran wax, polyglycerolated beeswax, octacosanyl stearate, ceresin wax, $C_{20}$-$C_{40}$ alkyl (hydroxystearyloxy)stearate waxes, polyethylene alcohol wax, Fischer-Tropsch wax, the waxes obtained by hydrogenation of castor oil esterified with cetyl alcohol, ouricury wax, montan wax, the glyceryl trihydroxystearate whose INCI name is Trihydroxystearin (sold, for example, by Elementis under the name Thixcin R), and mixtures thereof.

The total amount of waxes, including waxes having a melting point of at least 60° C. in the makeup removing composition, if present, can vary but is typically is about 0.01 to about 25 wt. %, based on the total weight of the makeup removing composition. In some cases, the total amount of waxes having a melting point of at least 60° C. may be about 0.01 to about 20 wt. %, about 0.01 to about 15 wt. %, about 0.01 to about 10 wt. %, about 0.01 to about 8 wt. %, about 0.1 to about 20 wt. %, about 0.1 to about 15 wt. %, about 0.1 to about 10 wt. %, or about 0.1 to about 8 wt. %, about 1 to about 20 wt. %, about 1 to about 15 wt. %, about 1 to about 10 wt. %, or about 1 to about 8 wt. %, based on the total weight of the makeup removing composition.

Similarly, the total amount of waxes having a melting point of at least 60° C. in the makeup removing composition, if present, can vary but is typically is about 0.01 to about 25 wt. %, based on the total weight of the makeup removing composition. In some cases, the total amount of waxes having a melting point of at least 60° C. may be about 0.01 to about 20 wt. %, about 0.01 to about 15 wt. %, about 0.01 to about 10 wt. %, about 0.01 to about 8 wt. %, about 0.1 to about 20 wt. %, about 0.1 to about 15 wt. %, about 0.1 to about 10 wt. %, or about 0.1 to about 8 wt. %, about 1 to about 20 wt. %, about 1 to about 15 wt. %, about 1 to about 10 wt. %, or about 1 to about 8 wt. %, based on the total weight of the makeup removing composition.

In some instances, the makeup removing compositions include one or more polyglycerol esters and one or more waxes having a melting point of greater than or equal to 60° C. The polyglycerol esters and the waxes having a melting point of greater than or equal to 60° C. may be selected from the those set forth above, and may be, for example, polyglyceryl-6 polyricinoleate and trihydroxystearin.

Surfactants

The makeup removing compositions typically include one or more surfactants. The surfactants may be nonionic, anionic, cationic, amphoteric (zwitterionic), or a mixture thereof. Typically, the makeup removing compositions include at least one or more nonionic surfactants, for example, one or more fatty acid esters, for example glyceryl fatty acid esters and/or non-glyceryl fatty acid esters.

The total amount of all types of surfactants in the makeup removing compositions can vary but is typically about 1 to about 70 wt. %, based on the total weight of the makeup removing composition. In some instances, the total amount of surfactants is about 1 to about 60 wt. %, about 1 to about 55 wt. %, about 5 to about 70 wt. %, about 5 to about 60 wt. %, about 5 to about 55 wt. %, about 10 to about 70 wt %, about 10 to about 60 wt. %, about 10 to about 55 wt. %, about 20 to about 70 wt. %, about 20 to about 60 wt. %, about 20 to about 55 wt. %, about 30 to about 70 wt. %, about 30 to about 60 wt. %, about 30 to about 55 wt. %, about 40 to about 70 wt. %, about 40 to about 60 wt. %, or about 40 to about 55 wt. %, based on the total weight of the makeup removing composition.

The total amount of nonionic surfactants in the makeup removing compositions can vary but is typically about 1 to about 70 wt. %, based on the total weight of the makeup removing composition. In some instances, the total amount of nonionic surfactants is about 1 to about 60 wt. %, about 1 to about 55 wt. %, about 5 to about 70 wt. %, about 5 to about 60 wt. %, about 5 to about 55 wt. %, about 10 to about 70 wt %, about 10 to about 60 wt. %, about 10 to about 55 wt. %, about 20 to about 70 wt. %, about 20 to about 60 wt. %, about 20 to about 55 wt. %, about 30 to about 70 wt. %, about 30 to about 60 wt. %, about 30 to about 55 wt. %, about 40 to about 70 wt. %, about 40 to about 60 wt. %, or about 40 to about 55 wt. %, Non-limiting examples of fatty acid esters include glyceryl fatty acid esters such as glyceryl monopalmitate, glyceryl monostearate, glyceryl monobehenate, and a mixture thereof.

The total amount of glyceryl fatty acids esters can vary but is typically about 0.1 to about 25 wt. %, about 0.1 to about 20 wt. %, about 0.1 to about 15 wt. %, about 0.1 to about 10 wt. %, about 0.5 to about 25 wt. %, about 0.5 to about 20 wt. %, about 0.5 to about 15 wt. %, about 0.5 to about 10 wt. %, about 1 to about 25 wt. %, about 1 to about 20 wt. %, about 1 to about 15 wt. %, about 1 to about 10 wt. %, or about 2 to about 8 wt. %, based on the total weight of the makeup removing composition.

The makeup removing compositions may alternatively or additionally include one or more non-glyceryl fatty acid esters. Non-limiting examples of non-glyceryl fatty acid esters include diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethyl hexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

The total amount of non-glyceryl fatty acid esters in the makeup removing compositions can vary but is typically about 1 to about 70 wt. %, based on the total weight of the makeup removing composition. In some instances, the total amount of non-glyceryl fatty acid esters is about 1 to about 60 wt. %, about 1 to about 55 wt. %, about 5 to about 70 wt. %, about 5 to about 60 wt. %, about 5 to about 55 wt. %, about 10 to about 70 wt %, about 10 to about 60 wt. %, about 10 to about 55 wt. %, about 20 to about 70 wt. %, about 20 to about 60 wt. %, about 20 to about 55 wt. %, about 30 to about 70 wt. %, about 30 to about 60 wt. %, about 30 to about 55 wt. %, about 40 to about 70 wt. %, about 40 to about 60 wt. %, or about 40 to about 55 wt. %, based on the total weight of the makeup removing composition.

In some instances, it is preferable that the makeup removing compositions include one or more glyceryl fatty acid esters and one or more non-glyceryl fatty acid ester, for example, glyceryl monosterate and ethylhexyl palmitate.

A more exhaustive but non-limiting list of nonionic surfactants that may be used in the makeup removing compositions are described later, under the heading, "Nonionic surfactants."

Forms

The makeup removing compositions may be in a variety of different forms, for example, a balm, a gel, a lotion, a cream, or a paste. In some cases, the makeup removing composition is preferably in the form of a balm, in particular a balm for removing makeup from the lips (lipstick). Most preferably, the makeup removing compositions of the instant case are anhydrous lipstick removing compositions, in the form of a balm.

The viscosity of the makeup removing compositions may vary, but in some instances, may be from about 2000 cps to about 250,000 cps at 32° C. In some cases, the viscosity may be from about 5000 to about 250,000 cps, from about 10,000 to about 250,000 cps, from about 25,000 to about 250,000 cps, from about 50,000 to about 250,000 cps, from about 100,000 cps to about 250,000 cps, from about 2000 cps to about 200,000 cps, from about 5000 to about 200,000 cps, from about 10,000 to about 200,000 cps, from about 25,000 to about 200,000 cps, from about 50,000 to about 200,000 cps, or from about 100,000 to about 250,000 cps at 32° C. The viscosity may be measured using, for example, TA Instrument's Discover Rheometer with a 40 mm diameter 1.99° cone Peltier steel plate. The viscosity may be measured from 0.3 to 2600 $s^{-1}$ shear rates, and using a linear best-fit line of a logarithmic plot of the data, the viscoscity at 0.1 $s^{-1}$ can be determined by extrapolation.

Methods

The makeup removing compositions are useful in methods for removing makeup from the body, in particular the face, including the lips. The user can simply apply the makeup removing compositions to an area of the body having makeup applied thereon, and subsequently remove the composition along with the makeup, for example, by wiping it away with a tissue or rinsing it away with water (or both). The user can also gently massage or rub the makeup removing composition on the skin to help facilitate the makeup removing action and enhance the exfoliation process.

More specifically, the methods of the instant disclosure include:
  a. applying a makeup removing composition of the instant disclosure to skin upon which makeup is adhered, for example, the lips upon which lipstick is adhered;
  b. sufficiently rubbing or massaging the makeup removing composition to at least partially delaminate the makeup, for example, lipstick; and
  c. removing at least a portion of the makeup removing composition and the delaminated makeup from the skin.

The methods effectively remove makeup from the skin, for example lipstick from the lips. The methods also exfoliate the skin, including the skin of the lips. Additionally, the methods hydrate the skin, including the skin of the lips. Thus, the methods of the instant disclosure include methods for removing makeup, methods for exfoliating the skin, and/or methods for hydrating the skin. Preferably, the methods remove makeup from skin while simultaneously exfoliating and hydrating the skin.

The rubbing and/or massaging of the makeup removing composition on the skin to which makeup is applied can be carried out, for example, by using one's fingers. Furthermore, when the makeup removing composition is used on the lips, the rubbing and/or massaging of the makeup removing composition on the lips can be carried out by simply rubbing one's lips together.

The removal of at least a portion of the makeup removing composition can be carried out by simply wiping away the composition from the skin, for example, using a tissue. The removal may also be carried out with rinsing with water, or by employing water and wiping.

EMBODIMENTS

In some embodiments, the makeup removing compositions are free or essentially free of silicones, for example, dimethicone, amodimethicone, cyclomethicone, etc. Similarly, in some instances, the makeup removing compositions are free or essentially free of petroleum-based products, for example, petrolatum, mineral oil, etc. Moreover, the makeup removing compositions may be free or essentially free of petrochemicals, phosphates, silicates, synthetic preservatives, synthetic perfumes, synthetic colorings, betaines, sulfate-based surfactants, and/or parabens, etc.

In certain embodiments, the makeup removing compositions of the instant disclosure are anhydrous and comprise, consist essentially of, or consists of:
  (a) about 1 to about 50 wt. %, preferably about 5 to about 40 wt. %, more preferably about 10 to about 35 wt. % of exfoliating particles, for example, particles that are insoluble in a fatty or oily medium but are soluble in water, such as sugar and/or salt particles;
  (b) about 1 to about 50 wt. %, preferably about 2 to about 40 wt. %, more preferably about 5 to about 35 wt. % of glycerin;
  (c) about 1 to about 50 wt. %, preferably, about 2 to about 25 wt. %, more preferably about 5 to about 15 wt. % of one or more natural fatty compounds, for example, one or more natural oils, one or more polyglycerol esters, one or more waxes (in particular one or more waxes having a melting point of at least 60° C.), and a mixture thereof; and
  (d) about 25 to about 75 wt. %, more preferably, about 30 to about 70 wt. %, more preferably about 35 to about 65 wt. % of one or more nonionic surfactants, for example, one or more glyceryl fatty acid esters, one or more non-glyceryl fatty acid esters, or a mixture thereof;

wherein the weight percentages are based on the total weight of the composition.

The makeup removing composition may be free or essentially free of silicones, for example, dimethicone, amodimethicone, cyclomethicone, etc. Similarly, in some instances, the makeup removing composition may be free or essentially free of petroleum-based products, for example, petrolatum, mineral oil, etc. Moreover, the makeup removing composition may be free or essentially free of petrochemicals, phosphates, silicates, synthetic preservatives, synthetic perfumes, synthetic colorings, betaines, sulfate-based surfactants, and/or parabens, etc.

The makeup removing composition may be a natural makeup removing composition, i.e., it may include only natural ingredients as defined herein.

The makeup removing composition may be in the form of a balm, a gel, a lotion, a cream, or a paste, preferably a balm. The makeup removing composition is preferably an anhydrous lipstick removing composition in the form of a balm.

The viscosity of the makeup removing composition may vary, but in some instances, may be from about 2000 cps to about 250,000 cps at 32° C. In some cases, the viscosity may be from about 10,000 to about 250,000 cps, from about 50,000 to about 250,000 cps, from about 100,000 cps to about 250,000 cps, from about 2000 cps to about 200,000 cps, from about 10,000 to about 200,000 cps, from about 50,000 to about 200,000 cps, or from about 100,000 to about 250,000 cps at 32° C. The viscosity may be measured using, for example, TA Instrument's Discover Rheometer. When the makeup removing composition is in the form of a balm, the viscosity is preferably from about 100,000 cps to about 250,000 cps, from about 100,000 to about 200,000 cps, or about 150,000 to about 200,000 cps at 32° C.

In some embodiments, the makeup removing composition is anhydrous and comprises, consist essentially of, or consists of:
(a) about 1 to about 50 wt. %, preferably about 5 to about 40 wt. %, more preferably about 10 to about 35 wt. % of exfoliating particles of sugar, for example, sucrose;
(b) about 1 to about 50 wt. %, preferably about 2 to about 40 wt. %, more preferably about 5 to about 35 wt. % of glycerin;
(c) about 1 to about 50 wt. %, preferably, about 2 to about 25 wt. %, more preferably about 5 to about 15 wt. % of two or more natural fatty compounds, the two or more natural fatty compounds comprising:
  (i) about 0.1 to about 20 wt. %, preferably about 0.5 to about 15 wt. %, more preferably about 1 to about 10 wt. % of one or more polyglycerol esters; and
  (ii) about 0.1 to about 20 wt. %, preferably about 0.5 to about 15 wt. %, more preferably about 1 to about 10 wt. % of one or more waxes having a melting point of greater than or equal to 60° C.; and
  (iii) optionally, about 0.01 to about 20 wt. %, preferably about 0.05 to about 15 wt. %, more preferably about 0.1 to about 10 wt. % of one or more natural oils;
(d) about 25 to about 75 wt. %, more preferably, about 30 to about 70 wt. %, more preferably about 35 to about 65 wt. % of two or more nonionic surfactants, the two or more nonionic surfactants comprising:
  (i) about 0.1 to about 20 wt. %, preferably about 0.5 to about 15 wt. %, more preferably about 1 to about 10 wt. % of one or more glyceryl fatty acid esters; and
  (ii) about 0.1 to about 70 wt. %, preferably about 0.5 to about 65 wt. %, more preferably about 1 to about 60 wt. %, and even more preferably about 20 to about 60 wt. % of one or more non-glyceryl fatty acid esters;
  wherein the weight percentages are based on the total weight of the composition and the composition is anhydrous.

The makeup removing composition may be free or essentially free of silicones, for example, dimethicone, amodimethicone, cyclomethicone, etc. Similarly, in some instances, the makeup removing composition may be free or essentially free of petroleum-based products, for example, petrolatum, mineral oil, etc. Moreover, the makeup removing composition may be free or essentially free of petrochemicals, phosphates, silicates, synthetic preservatives, synthetic perfumes, synthetic colorings, betaines, sulfate-based surfactants, and/or parabens, etc.

The makeup removing composition may be a natural makeup removing composition, i.e., it may include only natural ingredients, as defined herein.

The makeup removing composition may be in the form of a balm, a gel, a lotion, a cream, or a paste, preferably a balm. The makeup removing composition is preferably a lipstick removing composition in the form of a balm.

The viscosity of the makeup removing composition may vary, but in some instances, may be from about 2000 cps to about 250,000 cps at 32° C. In some cases, the viscosity may be from about 10,000 to about 250,000 cps, from about 50,000 to about 250,000 cps, from about 100,000 cps to about 250,000 cps, from about 2000 cps to about 200,000 cps, from about 10,000 to about 200,000 cps, from about 50,000 to about 200,000 cps, or from about 100,000 to about 250,000 cps at 32° C. The viscosity may be measured using, for example, TA Instrument's Discover Rheometer. When the makeup removing composition is in the form of a balm, the viscosity is preferably from about 100,000 cps to about 250,000 cps, from about 100,000 to about 200,000 cps, or about 150,000 to about 200,000 cps at 32° C.

In some embodiments, the makeup removing composition is a natural anhydrous lipstick removing composition in the form of a balm comprising, consisting essentially of, or consisting of:
(a) about 1 to about 50 wt. %, preferably about 5 to about 40 wt. %, more preferably about 10 to about 35 wt. % of exfoliating particles of sucrose;
(b) about 1 to about 50 wt. %, preferably about 2 to about 40 wt. %, more preferably about 5 to about 35 wt. % of glycerin;
(c) about 1 to about 50 wt. %, preferably, about 2 to about 25 wt. %, more preferably about 5 to about 15 wt. % of two or more natural fatty compounds, the two or more natural fatty compounds comprising:
  (i) about 0.1 to about 20 wt. %, preferably about 0.5 to about 15 wt. %, more preferably about 1 to about 10 wt. % of one or more polyglycerol esters; and
  (ii) about 0.1 to about 20 wt. %, preferably about 0.5 to about 15 wt. %, more preferably about 1 to about 10 wt. % of one or more waxes having a melting point of greater than or equal to 60° C.; and
  (iii) optionally, about 0.01 to about 20 wt. %, preferably about 0.05 to about 15 wt. %, more preferably about 0.1 to about 10 wt. % of one or more natural oils;
(d) about 25 to about 75 wt. %, more preferably, about 30 to about 70 wt. %, more preferably about 35 to about 65 wt. % of two or more nonionic surfactants, the two or more nonionic surfactants comprising:

(i) about 0.1 to about 20 wt. %, preferably about 0.5 to about 15 wt. %, more preferably about 1 to about 10 wt. % of one or more glyceryl fatty acid esters; and (ii) about 0.1 to about 70 wt. %, preferably about 0.5 to about 65 wt. %, more preferably about 1 to about 60 wt. %, and even more preferably about 20 to about 60 wt. % of one or more non-glyceryl fatty acid esters;

wherein the weight percentages are based on the total weight of the composition, and the composition has a viscosity of about 100,000 cps to about 250,000 cps, preferably from about 100,000 to about 200,000 cps, more preferably from about 150,000 to about 200,000 cps at 32° C.

The polyglycerol esters of (c)(i) may be selected from Polyglyceryl-4 Caprate, Polyglyceryl-2 Caprate, Polyglyceryl-4 Caprylate, Polyglyceryl-6 Caprylate, Polyglyceryl-6 Caprate, Polyglyceryl-4 Caprylate/Caprate, Polyglyceryl-6 Caprylate/Caprate, Polyglyceryl-3 Cocoate, Polyglyceryl-4 Cocoate, Polyglyceryl-10 Decalinoleate, Polyglyceryl-10 Decaoleate, Polyglyceryl-10 Decacasterate, Polyglyceryl-3 Dicaprate, Polyglyceryl-3 Dicocoate, Polyglyceryl-10 Didecanoate, Polyglyceryl-2 Diisostearate, Polyglyceryl-3 Diisostearate, Polyglyceryl-10 Diisostearate, Polyglyceryl-4 Dilaurate, Polyglycerin-2 Dioleate, Polyglyceryl-3 Dioleate, Polyglyceryl-6 Dioleate, Polyglyceryl-10 Dioleate, Polyglyceryl-6 Dipalmitate, Polyglyceryl-10 Dipalmitate, Polyglyceryl-2 Dipolyhydroxystearate, Polyglyceryl-2 Distearate, Polyglyceryl-3 Distearate, Polyglyceryl-6 Distearate, Polyglyceryl-10 Distearate, Polyglyceryl-10 Heptaoleate, Polyglyceryl-10 Heptastearate, Polyglyceryl-6 Hexaoleate, Polyglyceryl-10 Hexaoleate, Polyglyceryl-2 Isopalmitate, Polyglyceryl-2 Isostearate, Polyglyceryl-4 Isostearate, Polyglyceryl-5 Isostearate, Polyglyceryl-6 Isostearate, Polyglyceryl-10 Isostearate, Polyglyceryl-2 Laurate, Polyglyceryl-3 Laurate, Polyglyceryl-4 Laurate, Polyglyceryl-4 Laurate/Sebacate, Polyglyceryl-4 Laurate/Succinate, Polyglyceryl-5 Laurate, Polyglyceryl-6 Laurate, Polyglyceryl-10 Laurate, Polyglyceryl-3 Myristate, Polyglyceryl-10 Myristate, Polyglyceryl-2 Oleate, Polyglyceryl-3 Oleate, Polyglyceryl-4 Oleate, Polyglyceryl-5 Oleate, Polyglyceryl-6 Oleate, Polyglyceryl-8 Oleate, Polyglyceryl-10 Oleate, Polyglyceryl-3 Palmitate, Polyglyceryl-6 Palmitate, Polyglyceryl-10 Pentalaurate, Polyglyceryl-10 Pentalinoleate, Polyglyceryl-4 Pentaoleate, Polyglyceryl-10 Pentaoleate, Polyglyceryl-3 Pentaricinoleate, Polyglyceryl-6 Pentaricinoleate, Polyglyceryl-10 Pentaricinoleate, Polyglyceryl-4 Pentastearate, Polyglyceryl-6 Pentastearate, Polyglyceryl-10 Pentastearate, Polyglyceryl-3 Polyrisinoleate, Polyglyceryl-6 Polyricinoleate, Polyglyceryl-3 Ricinoleate, Polyglyceryl-2 Sesquiisostearate, Polyglyceryl-2 Sesquioleate, Polyglyceryl-2 Sesquistearate, Polyglyceryl-3 Stearate, Polyglyceryl-2 Stearate, Polyglyceryl-4 Stearate, Polyglyceryl-8 Stearate, Polyglyceryl-10 Stearate, Polyglyceryl-2 Tetraisostearate, Polyglyceryl-6 Tetraoleate, Polyglyceryl-10 Tetraoleate, Polyglyceryl-2 Tetrastearate, Polyglyceryl-2 Triisostearate, Polyglyceryl-3 Triisostearate, Polyglyceryl-10 Trioleate, Polyglyceryl-4 Tristearate, Polyglyceryl Tristearate, Polyglyceryl-10 Tristearate, and mixtures thereof, preferably the polyglyceryl ester is polyglyceryl-6 polyricinoleate.

The waxes having a melting point of at least 60° C. of (c)(ii) may be selected from from carnauba wax, ozokerite, microcrystalline wax, 12-hydroxystearic acid, a polyethylene wax, polymethylene waxes, beeswax, candelilla wax, hydroxyoctacosanyl hydroxystearate, hydrogenated castor oil, hydrogenated jojoba oil, rice bran wax, polyglycerolated beeswax, octacosanyl stearate, ceresin wax, C20-C40 alkyl (hydroxystearyloxy)stearate waxes, 12-hydroxystearic acid, polyethylene alcohol wax, Fischer-Tropsch wax, ouricury wax, trihydroxystearin, and a mixture thereof, preferably trihydroxystearin.

The glyceryl fatty acid esters of (d)(ii) may be selected from glyceryl monopalmitate, glyceryl monostearate, and glyceryl monobehenate, and a mixture thereof.

The non-glyceryl fatty acid esters of (d)(iii) may be selected from diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof, preferably ethylhexyl palmitate.

Nonionic Surfactants

Examples of nonionic surfactants that may be used are described, for example, in the Handbook of Surfactants by M. R. Porter, published by Blackie & Son (Glasgow and London), 1991, pp. 116-178, which is incorporated herein by reference in its entirety. The nonionic surfactant may be alcohols, alpha-diols and ($C_1$-$C_{24}$)alkylphenols, these compounds being polyethoxylated, polypropoxylated and/or polyglycerolated, and containing at least one fatty chain comprising, for example, from 8 to 18 carbon atoms, it being possible for the number of ethylene oxide and/or propylene oxide groups to especially range from 2 to 50, and for the number of glycerol groups to especially range from 2 to 30.

Mention may also be made of copolymers of ethylene oxide and propylene oxide, optionally oxyethylenated sorbitan fatty acid esters, sucrose fatty acid esters, polyoxyalkylenated fatty acid esters, polyoxyalkylenated fatty amides, optionally oxyalkylenated alkyl(poly)glucosides, alkylglucoside esters, derivatives of N-alkylglucamine and of N-acylmethylglucamine, aldobionamides, amine oxides and (poly)oxyalkylenated silicones.

The nonionic surfactants are more particularly chosen from monooxyalkylenated or polyoxyalkylenated and monoglycerolated or polyglycerolated nonionic surfactants, and alkyl(poly)glucosides. The oxyalkylene units are more particularly oxyethylene or oxypropylene units, or a combination thereof, preferably oxyethylene units.

Useful nonionic surfactants may include: oxyalkylenated ($C_8$-$C_{24}$)alkylphenols; saturated or unsaturated, linear or branched, oxyalkylenated $C_8$-$C_{40}$ alcohols; saturated or unsaturated, linear or branched, oxyalkylenated $C_8$-$C_{30}$ amides; esters of saturated or unsaturated, linear or branched, $C_8$-$C_{30}$ acids and of polyethylene glycols; saturated or unsaturated, oxyethylenated plant oils; condensates of ethylene oxide and/or of propylene oxide, alone or as mixtures; oxyethylenated and/or oxypropylenated silicones; and alkyl(poly)glucosides.

As examples of monoglycerolated or polyglycerolated nonionic surfactants, monoglycerolated or polyglycerolated $C_8$-$C_{40}$ alcohols are useable. In particular, the monoglycerolated or polyglycerolated C $C_8$-$C_{40}$ alcohols correspond to formula (VIII) below:

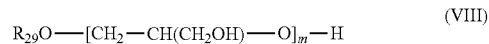

(VIII)

in which formula (VIII):

$R_{29}$ represents a linear or branched $C_8$-$C_{40}$ and preferably $C_8$-$C_{30}$ alkyl or alkenyl radical; and m represents a number ranging from 1 to 30, or from 1 to 10.

As examples of compounds of formula (VIII), mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol of formula (VIII) may represent a mixture of alcohols in the same way that the value of m represents a statistical value, which means that, in a commercial product, several species of polyglycerolated fatty alcohols may coexist in the form of a mixture.

The alkyl(poly)glycoside nonionic surfactant(s) may be represented by formula (IX) below:

$$R_{30}O\text{---}(R_{31}O)_t(G)_v \quad (IX)$$

in which:

$R_{30}$ represents a saturated or unsaturated, linear or branched alkyl group comprising from about 8 to 24 carbon atoms, or an alkylphenyl group in which the linear or branched alkyl group comprises from 8 to 24 carbon atoms;

$R_{31}$ represents an alkylene group containing from about 2 to 4 carbon atoms, G represents a saccharide unit comprising from 5 to 6 carbon atoms, t denotes a value ranging from 0 to 10, or from 0 to 4, and v denotes a value ranging from 1 to 15.

In some cases, the alkyl(poly)glycoside nonionic surfactant(s) correspond to formula (IX) in which:

$R_{30}$ denotes a linear or branched, saturated or unsaturated alkyl group containing from 8 to 18 carbon atoms, G denotes glucose, fructose or galactose, preferably glucose, t denotes a value ranging from 0 to 3, and is preferably equal to 0, and $R_{31}$ and v are as defined previously.

The degree of polymerization of the alkyl(poly)glucoside nonionic surfactant(s), as represented, for example, by the index v in formula (IX), ranges on average from 1 to 15, or from 1 to 4. This degree of polymerization more particularly ranges from 1 to 2 and better still from 1.1 to 1.5, on average.

The glycoside bonds between the saccharide units are of 1.6 or 1.4 type and preferably of 1.4 type.

Examples of compounds of formula (IX) that may especially be mentioned are the products sold by the company Cognis under the names Plantaren® (600 CS/U, 1200 and 2000) or Plantacare® (818, 1200 and 2000). Use may also be made of the products sold by the company SEPPIC under the names Triton CG 110 (or Oramix CG 110) and Triton CG 312 (or ORAMIX NS 10), the products sold by the company BASF under the name Lutensol GD 70 or the products sold by the company Chem Y under the name AG10 LK. Use may also be made, for example, of the 1,4-($C_8$-$C_{16}$)alkyl-polyglucoside as an aqueous solution at 53% by weight relative to the total weight of the solution, sold by Cognis under the reference Plantacare 818 UP.

Implementation of the present disclosure is provided by way of the following examples. The examples serve to illustrate the technology without being limiting in nature.

Example 1

| | (Inventive Compositions) | | | | |
|---|---|---|---|---|---|
| | INCI US | A | B | C | D |
| Exfoliating Particles | SUCROSE | 25 | 27 | 25 | 29.4 |
| Solvent | GLYCERIN | 12.8 | 15.9 | 22.3 | 8.6 |
| Fatty Compounds | POLYGLYCERYL-6 POLYRICINOLEATE | 3 | 2.2 | 2 | 2.4 |
| | TRIHYDROXYSTEARIN | 5 | 2.7 | 2.5 | 2.9 |
| | MENTHA PIPERITA (PEPPERMINT) OIL | 0.3 | 0.3 | 0.3 | 0.3 |
| Nonionic Surfactants | ETHYLHEXYL PALMITATE | 49 | 48.7 | 45 | 52.9 |
| | GLYCERYL STEARATE | 5 | 3.2 | 3 | 3.5 |
| Optional Components | FRAGRANCE AND/OR DYES/PIGMENT | ≤1 | ≤1 | ≤1 | ≤1 |
| Optional Components | PRESERVATIVES AND/OR ANTIOXIDANTS | ≤2 | ≤2 | ≤2 | ≤2 |

The viscosity of the compositions was measured using TA Instrument's Discover Rheometer with a heated stage set to 32° C. The data was collected with a 40 mm diameter 1.99° cone Peltier steel plate. The viscosity was measured from 0.3 to 2600 $s^{-1}$ shear rates. Using a linear best-fit line of a logarithmic plot of the data, the viscosity at 0.1 $s^{-1}$ was extrapolated, and found to be between about 150,000 cps to about 200,000 cps.

Example 2

| | (Comparative Compositions) | | | |
|---|---|---|---|---|
| | INCI US | E | F | G |
| Exfoliating Particles | SUCROSE | | 13.4 | 35 |
| | THEOBROMA GRANDIFLORUM SEED POWDER | | 0.2 | |
| Solvent | GLYCERIN | | | 62.2 |
| | POLYGLYCERIN-3 | 0.1 | | |
| | ALCOHOL | | | 0.2 |
| | CAPRYLYL GLYCOL | | 0.3 | |
| Fatty Compounds | TRIHYDROXYSTEARIN | | 6 | |
| | ACACIA DECURRENS FLOWER WAX | 0.1 | | |
| | BUTYROSPERMUM PARKII (SHEA) BUTTER | 2 | | |
| | ISOPROPYL PALMITATE | | 45.7 | |
| | OCTYLDODECANOL | 20 | | |
| | PRUNUS ARMENIACA (APRICOT) KERNEL OIL | | 2 | |
| | GLYCINE SOJA (SOYBEAN) OIL | | 6 | |
| | COCOS NUCIFERA (COCONUT) OIL | | 0.1 | |
| | HELIANTHUS ANNUUS (SUNFLOWER) SEED WAX | 1 | | |
| | JOJOBA ESTERS | 1.8 | | |
| | SYNTHETIC WAX | | 7 | |
| | PETROLATUM | 10 | | |
| | BEESWAX | 11 | 1.5 | |
| | THEOBROMA CACAO (COCOA) SEED BUTTER | | 0.01 | |
| Nonionic Surfactants | ETHYLHEXYL PALMITATE | 41 | | |
| | GLYCERYL STEARATE | | 6 | |
| | PEG-7 GLYCERYL COCOATE | | 5 | |
| Polymers | XANTHAN GUM | | | 0.2 |

-continued (Comparative Compositions)

| | INCI US | E | F | G |
|---|---|---|---|---|
| | SODIUM CARBOXYMETHYL STARCH | | | 2.4 |
| | POLYETHYLENE | 10 | | |
| Fillers | PERLITE AND/OR SILICA | 3 | 3.5 | |
| Optional Components | FRAGRANCE AND/OR DYES/PIGMENT | ≤1 | ≤1 | ≤1 |
| Optional Components | PRESERVATIVES AND/OR ANTIOXIDANTS, ETC. | ≤2 | ≤2 | ≤2 |

Example 3

Hydrating Properties

Testing was carried out to determine the hydrating properties of inventive compositions. Participants of the study refrained from using any moisturizer on their forearms for three days prior to the start of the study. On the day of evaluation, the volar forearms of the participants were cleansed with one 70% isopropyl alcohol wipe and the skin was allowed to air dry for thirty (30) minutes prior to baseline measurements. Six (6) total 2 cm×2 cm square test sites were marked across of the participants' volar forearms using a skin marker—3 sites on each forearm. Test sites were placed at least 2 cm from both the wrist and elbow. Baseline measurements of each site were taken with a Corneometer 825. Three (3) measurements were taken from each site (corneometer) and any outlier measurements (greater than 10 points) will were retaken.

Eight milligrams (2 mg/cm$^2$*4 cm$^2$=8 mg) of a product was applied to the test sites using a micro-pipette and the product was spread evenly across the test site with a glass rod. The products tested included Inventive Compositions B, C, and D from Example 1, Comparative Composition E of Example 2, and a "Control" composition, which is an internal standard used to confirm properly functioning of equipment. After application of a product to a test site, the product was dry-wiped using a small lint-free Kimtech "Delicate Task Wipers" Kimwipe, with one soft stroke in each of four primary directions (up, down, left, right). Measurements were taken from each site at 15 minutes, 1 hour, 2 hours, and 6 hours after product application. The results are presented in the table below.

| | Baseline | T$_1$ (15 min) | T$_2$ (1 hr) | T$_3$ (2 hr) | T$_4$ (6 hr) |
|---|---|---|---|---|---|
| Comparative E 0% glycerin | 32.8 ± 5.1 | 38.8 ± 7.9 | 36.5 ± 7.2 | 35.4 ± 7.7 | 34.0 ± 7.5 |
| Inventive B 14.7% glycerin | 33.1 ± 6.5 | 45.2 ± 9.1 | 43.8 ± 11 | 40.7 ± 8.5 | 38.2 ± 8.3 |
| Inventive C 22.5% glycerin | 34.1 ± 5.3 | 47.4 ± 8.2 | 45.9 ± 9.5 | 43.5 ± 8.2 | 40.0 ± 8.1 |
| Inventive D 7.3% glycerin | 34.8 ± 6.1 | 47.0 ± 7.9 | 46.2 ± 10.2 | 42.4 ± 9.2 | 41.0 ± 8.7 |
| Bare | 35.2 ± 6.4 | 33.8 ± 8.0 | 34.0 ± 5.8 | 34.3 ± 5.8 | 35.1 ± 5.8 |
| Control | 35.1 ± 6.6 | 47.0 ± 8.0 | 45.5 ± 9.0 | 42.1 ± 7.3 | 40.0 ± 7.8 |

The data show that the inventive compositions provided a statistically significant degree of hydration to the lips at all time points (from 15 minutes to 6 hours). Comparative Composition E provided a statistically significant improvement in hydration at 15 minutes and 1 hour, but not at 2 hours and 6 hours. Thus, the inventive compositions were effective in hydrating the lips and the hydrating effects lasted for a surprisingly long period time (for at least 6 hours).

Example 4

Lipstick Removal Efficiency

The lipstick removal efficiency of Inventive Composition A was tested and compared with Comparative Compositions E, F, and G. A commercial lipstick that is advertised as "long-lasting" was applied to abrasion paper to form a 1 mm thick film on the abrasion paper. The lipstick was allowed to dry on the abrasion paper overnight at 25° C. in a humidity chamber (60% RH). The abrasion paper was cut into strips having a width of 2 cm. A ring having a diameter of ½ inch was placed on each strip and 1 g of Inventive Composition A or Comparative Compositions E, F, or G, was placed into the ring. The tested compositions were pressed into the ring to ensure contact with the lipstick film on the abrasion paper.

The tested compositions were allowed to remain on the lipstick film for 1 minute. After 1 minute, a Kimwipe (Kimberly-Clark™ Professional Kimtech Science™ Kimwipes™) was used to wipe the entire length of the strip 10 times. After wiping, the strips were photographed and analyzed using ImageJ to determine the percentage of lipstick remaining in the ½ diameter ring that was treated with the test compositions. ImageJ is a Java-based image processing program developed at the National Institutes of Health and the Laboratory for Optical and Computational Instrumentation and is used in the art for analyzing images. The results are reported in the table below.

| | INVENTIVE A | COMPARATIVE E | COMPARATIVE F | COMPARATIVE G |
|---|---|---|---|---|
| Longwear Removal Efficiency | 69% | 31% | 82% | 2% |
| 4° C. Stability | Yes | Yes | No | Yes |
| Naturality | 100.00% | 57.00% | 86.37% | 99.97% |
| Hydration | 6+ hr | 1 hr | Not tested | Not tested |

Inventive Composition A removed 69% of the lipstick, which is more than double the amount of lipstick removed by Comparative Compositions E and G. Comparative Composition F removed 82% of the lipstick, but Comparative Composition F was not stable; Comparative Composition F became solid at 4° C. Stability was monitored for two months at 25° C., 45° C., and 4° C. The compositions were visually inspected and viscosity measurements taken at 1 week, 2 weeks, 4 weeks, and 8 weeks.

Separately, the compositions were subjected to two weeks of freeze-thaw cycling, wherein a freeze/thaw cycle was carried out by exposing the composition to freezing temperatures (approximately −15° C.±2° C.) for 24 hours and then subjecting the composition to room temperature (approximately 25° C.±2° C.) for 24 hours.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention. All of the compositions described throughout the disclosure may "comprise," "consist essentially of," of "consist of" the recited elements.

The terms "a," "an," and "the" are understood to encompass the plural as well as the singular.

Thus, the term "a mixture thereof" also relates to "mixtures thereof." Throughout the disclosure, the term "a mixture thereof" may be used following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−5% of the indicated number.

Some of the various categories of components identified for the cleansing compositions may overlap. In such cases where overlap may exist and the composition/product includes two overlapping components (or more than two overlapping components), an overlapping component does not represent more than one component. For example, a fatty acid may be defined as both a "fatty compound" and a "surfactant." If a particular composition/product includes both a fatty compound and an surfactant, a single fatty acid can serve as only a fatty compound or as only a surfactant (a single fatty acid does not serve as both the fatty compound and the surfactant).

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded. In other words, the compositions of the instant disclosure may be free or essentially free of any one or more of the components positively set forth in the instant disclosure.

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of less than 1% by weight does not materially affect the basic and novel characteristics of the claimed invention. Similarly, the compositions may include less than 0.5 wt. %, less than 0.1 wt. %, less than 0.05 wt. %, or less than 0.01 wt. %, or none of the specified material. Furthermore all components that are positively set forth in the instant disclosure may be negatively excluded from the claims, e.g., a claimed composition may be "free," "essentially free" (or "substantially free") of one or more components that are positively set forth in the instant disclosure.

The term "anhydrous" as used herein means that the compositions is "substantially free" or "essentially free" of water, i.e., the composition contains less than about 2% by weight of a water added to a composition, based on the total weight of the composition. Nonetheless, the compositions may include less than about 2 wt. % of water, based on the total weight of the cosmetic composition. The compositions may contain less than about 1 wt. %, less than about 0.5 wt. %, less than about 0.5 wt. %, less than about 0.1 wt. %, or no water.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A makeup removing composition comprising:
   a. about 1 to about 50 wt. % of exfoliating particles;
   b. about 1 to about 50 wt. % of glycerin;
   c. about 1 to about 50 wt. % of two or more natural fatty compounds comprising:
      (i) one or more polyglycerol esters; and
      (ii) one or more waxes having a melting point of greater than or equal to 60° C.; and
   d. about 25 to about 75 wt. % of one or more nonionic surfactants;
   wherein the weight percentages are based on the total weight of the composition and the composition is anhydrous.

2. The composition of claim 1, wherein the composition contains only natural ingredients.

3. The composition of claim 1, wherein the exfoliating particles are soluble in water but insoluble in oil.

4. The composition of claim 3, wherein the exfoliating particles are sugar particles, salt particles, or a mixture thereof.

5. The composition of claim 1, wherein the one or more waxes having a melting point of greater than or equal to 60° C. are selected from carnauba wax, ozokerite, microcrystalline wax, 12-hydroxystearic acid, a polyethylene wax, polymethylene waxes, beeswax, candelilla wax, hydroxyoctacosanyl hydroxystearate, hydrogenated castor oil, hydrogenated jojoba oil, rice bran wax, polyglycerolated beeswax, octacosanyl stearate, ceresin wax, C20-C40 alkyl (hydroxystearyloxy)stearate waxes, 12-hydroxystearic acid, polyethylene alcohol wax, Fischer-Tropsch wax, ouricury wax, trihydroxystearin, and a mixture thereof.

6. The composition of claim 1, wherein the one or more nonionic surfactants are selected from fatty acid esters.

7. The composition of claim 1, wherein the one or more nonionic surfactants are selected from glyceryl fatty acid esters.

8. The composition of claim 1, wherein the one or more glyceryl fatty acid esters are selected from glyceryl monopalmitate, glyceryl monostearate, and glyceryl monobehenate, and a mixture thereof.

9. The composition of claim 1, wherein the one or more nonionic surfactants are selected from non-glyceryl fatty acid esters.

10. The composition of claim 9, wherein the one or more non-glyceryl fatty acid esters are selected from diisopropyl adipate, dioctyl adipate, 2-ethylhexyl hexanoate, ethyl laurate, cetyl octanoate, octyldodecyl octanoate, isodecyl neopentanoate, myristyl propionate, 2-ethylhexyl 2-ethylhexanoate, 2-ethylhexyl octanoate, 2-ethylhexyl caprylate/caprate, methyl palmitate, ethyl palmitate, isopropyl palmitate, dicaprylyl carbonate, isopropyl lauroyl sarcosinate, isononyl isononanoate, ethylhexyl palmitate, isohexyl laurate, hexyl laurate, isocetyl stearate, isopropyl isostearate, isopropyl myristate, isodecyl oleate, glyceryl tri(2-ethylhexanoate), pentaerythrithyl tetra(2-ethylhexanoate), 2-ethylhexyl succinate, diethyl sebacate, and mixtures thereof.

11. The composition of claim 1, wherein the one or more nonionic surfactants include one or more glyceryl fatty acid esters and one or more non-glyceryl fatty acid esters.

12. The composition of claim 1, wherein the composition is essentially free of silicones.

13. A makeup removing composition comprising:
   a. about 5 to about 50 wt. % of exfoliating particles of sucrose;
   b. about 1 to about 30 wt. % of glycerin;
   c. about 1 to about 50 wt. % of two or more natural fatty compounds, the two or more natural fatty compounds comprising:
      (i) one or more polyglycerol esters; and
      (ii) one or more waxes having a melting point of greater than or equal to 60° C.; and
   d. about 25 to about 75 wt. % of two or more nonionic surfactants, the two or more nonionic surfactants comprising:
      (i) one or more glyceryl fatty acid esters; and
      (ii) one or more non-glyceryl fatty acid esters;
         wherein the weight percentages are based on the total weight of the composition and the composition is anhydrous.

14. A method for removing makeup from the skin and simultaneously exfoliating and hydrating the skin comprising:
   a. applying the makeup removing composition of claim 1 to skin upon which makeup is adhered;
   b. sufficiently rubbing or massaging the makeup removing composition in order to at least partially delaminate the makeup; and
   c. removing at least a portion of the makeup removing composition and the delaminated makeup from the skin.

15. The method of claim 14, wherein the skin is the skin of the lips.

16. The method of claim 14, wherein the makeup removing composition and the rubbing or massaging is carried using one's fingers.

17. The method of claim 14, wherein the makeup removing composition contains only natural ingredients.

* * * * *